United States Patent [19]

Tournier et al.

[11] Patent Number: 5,866,100

[45] Date of Patent: Feb. 2, 1999

[54] COMPOSITIONS FOR IMAGING OF THE GASTROINTESTINAL TRACT

[75] Inventors: Hervé Tournier, Valleiry; Philippe Bussat, Feigeres, both of France

[73] Assignee: Bracco Research S.A., Switzerland

[21] Appl. No.: 770,707

[22] Filed: Dec. 19, 1996

[30] Foreign Application Priority Data

Dec. 19, 1995 [EP] European Pat. Off. ............ 95810804

[51] Int. Cl.$^6$ .................................................. A61K 49/04
[52] U.S. Cl. .................................. 424/9.452; 424/9.454; 560/37; 560/43
[58] Field of Search ............................. 424/9.452, 9.454; 560/37, 43

[56] References Cited

U.S. PATENT DOCUMENTS

| | | | |
|---|---|---|---|
| 3,446,837 | 5/1969 | Wallingford | 260/471 |
| 3,453,322 | 7/1969 | Obendorf et al. | 260/518 |
| 3,484,481 | 12/1969 | Obendorf et al. | 260/518 |
| 3,702,866 | 11/1972 | Slavesen et al. | 260/501.11 |
| 3,953,501 | 4/1976 | Klieger et al. | 260/518 A |
| 4,001,323 | 1/1977 | Felder et al. | 260/559 A |
| 4,025,550 | 5/1977 | Obendorf et al. | 260/518 A |
| 4,584,401 | 4/1986 | Sovak et al. | 564/153 |
| 5,536,490 | 7/1996 | Klaveness et al. | 424/9.52 |

FOREIGN PATENT DOCUMENTS

| | | |
|---|---|---|
| 317867 | 9/1974 | Austria . |
| 122430 | 6/1971 | Norway . |
| 97/22365 A3 | 6/1977 | WIPO . |
| 92/17212 | 10/1992 | WIPO . |

OTHER PUBLICATIONS

Hoey, GB et al., Invest. Radiol 15(6 suppl.):s289–s295 (1980).

*Primary Examiner*—Gary E. Hollinden
*Attorney, Agent, or Firm*—Nixon & Vanderhye

[57] ABSTRACT

The invention relates to non-ionic triiodo aromatic compounds and compositions comprising triiodo aromatic polymers useful for X-ray imaging of gastro-intestinal tract. Disclosed compounds are acrylic acid esters of triiodobenzenes with a different degree of reticulation and their polymers/homopolymers. A method of making the polymers, method of making X-ray contrast agents using the polymers and use of the contrast agents is also disclosed.

19 Claims, 6 Drawing Sheets

COMPOSITIONS FOR IMAGING OF THE GASTROINTESTINAL TRACT

TECHNICAL FIELD

The invention relates to triiodobenzene derivatised compounds, compositions comprising triiodobenzene polymers useful for X-ray imaging of gastrointestinal tract, method of making the polymers, method of making X-ray contrast agents and use.

BACKGROUND ART

Barium sulphate, a widely used contrast agent for the imaging of the gastrointestinal tract over the years has been administered orally or rectally to millions of patients around the world. Relatively inexpensive, with negligible adsorption and speedy elimination from the body, barium sulphate, despite of its disadvantages, is still in use. Of unpleasant taste, poor adhesion to the luminal linings and insuficient homogeneity in the presence of gastric fluids, this contrast agent has been in use for almost 40 years since proposed alternatives, although off-setting some disadvantages, have not been able to provide GI tract contrast agent which will eliminate use of this otherwise not harmless chemical.

Due to their capacity to efficiently absorb X-rays, and thus generate very good contrasts, iodinated compounds have also been in use in X-ray imaging of gastrointestinal tract. So far, many proposals aiming at improved characteristics of formulations comprising these compounds have been made. Different formulations with lower toxicity, smoother passage through the GI tract, reduced number of undesired side effects, lower irritation of the intestinal mucosa, etc. have been suggested (see for example U.S. Pat. No. 3,360,436, U.S. Pat. No. 4,735,795 & U.S. Pat. No. 5,047,228).

Among different proposals, EP-A-0 436 316 (Sovak) discloses use of hydroxy amino-substituted triiodobenzoates with the remaining position substituted by amino or carboxy group. The compounds disclosed have low solubility in the GI tract and can be formulated and used as contrast agents for radiography of the GI tract. Addition polymers comprised of triiodo compounds bonded through an amino nitrogen to a non-oxo-carbonyl group have been proposed as compounds with low toxicity and improved osmolality vis-a-vis the tract. Compounds and polymers disclosed are obtained by O- or N- alkylation of sodium diatriazoate or triiodobenzoates to yield intermediates which are subsequently polymerized to produce polymers with the molecular weight of at least 50 kDaltons. In the sole example of acylation reaction, 5-amino-2,4,6-triiodo-isophtalic acid is converted to 5-N-acrylamido derivative by reacting acryloyl chloride with 2,3-dihydroxy-propyl 5-{N-(2,3-dihydroxy-propyl)-acetamido}-2,4,6-triiodo-3-{N-(methyl)carbamoyl}-benzoate in dry N,N-dimethyacetamide. All compounds disclosed are ionic in nature which means that they still have higher osmolality than non-ionic compounds.

Another approach has been disclosed in WO-A-93/10824. This document deals with macromolecular polyamine compounds which contain a number of aromatic iodinated molecules. The disclosure is based on use of polyamine polymers to which aromatic iodinated compounds are attached via a number of reaction routes to yield dendrimers useful for manufacture of injectable X-ray contrast agents. Dendrimers disclosed comprise as the backbone all known dense star polymers, dense star polyamines, starbust polymers, star combed-branched polyamines, etc.

Acylation of triiodophenol or iothalamic acid with methacryloyl or methacrylate derivatives has been described as a viable route to production of radiopaque implant materials. Visible in a non-invasive manner using routine X-ray absorption imaging technique, these materials have attracted certain interest in the recent times. Synthetic routes and different studies of these solid polymeric biomaterials are described by A. Jayakrishnan et al. in *Journ. Appl. Polymer Sci.* 44 (1992) 743, M. A. B. Kruft et al. *Journ. Bio. Mat. Res.* 28 (1994) 1259, D. Horak, *Biomat.* 8 (1987) 142, etc.

Thus over the years various improvements of X-ray contrast agents were made bringing different compositions closer to the desired contrast medium for GI tract examinations. However, none of the media presently available has properties which would make any of them to be a widely acceptable GI tract contrast agent. Ideally, contrast agent for GI tract would have negligible adsorption, speedy elimination from the body and the low cost of barium sulfate, would be easier to swallow (have lower vicosity and better i.e. less unpleasant taste), but would also be able to delineate intestinal wall detail, be inert to gastric pH, provide adequate opacificity and have differential affinity for the gastrointestinal mucosa.

SUMMARY OF THE INVENTION

Briefly summarized, the invention relates to iodinated aromatic compounds of the general formula (I):

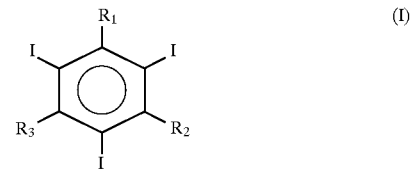

in which $R_1$, $R_2$ and $R_3$ are the same or different and are —$CON(R_4)R_5$ or —$N(R_4)$—CO—$R_6$ groups, where:

$R_4$—is H or a linear or branched alkyl residue ($C_1$–$C_6$), optionally substituted by 1–5 OH and/or alkoxy and/or hydroxyalkoxy groups, $R_5$—is a linear or branched alkyl residue ($C_2$–$C_6$), optionally substituted by 1–5 OH and/or alkoxy and/or hydroxyalkoxy groups or by one or two groups —NH—$COR_5$ or —CO—$N(R_4)R_5$, or $R_5$ is the residue of a carbohydrate, or $R_4$ and $R_5$ taken together, are alkylene, are an alkylene chain ($C_3$–$C_7$) which can be interupted by O, S, N, $R_6$—is a linear or branched alkyl residue ($C_1$–$C_6$), optionally substituted by 1–5 OH and/or alkoxy and/or hydroxyalkoxy groups and can also include an oxo group, in which at least one hydroxyl group is esterified with a substituted acrylic acid group of formula $C(R_7)_2$=$CR_8$—COOH wherein $R_7$— & $R_8$— are H or ($C_1$–$C_6$) alkyls said acrylic group being in polyacrylic form, i.e. in the form of polymers, homopolymers or copolymers with other olefinic monomers. These polymers showing high level of opacification and bioadhesivity are found particularly useful when used as X-ray contrast agents for the gastrointestinal tract.

Polymers and homopolymers produced from mixtures in which the molar ratio of the triiodobenzene compound to the acrylic monomer is between 1:1 and 1:3 are particularly suitable for the manufacture of X-ray contrast agents of the invention. In the form of viscous aqueous solutions or gels, the polymerized acrylic esters of triiodobenzenes exhibit high opacification and bioadhesivity. Both properties are very desirable in contrast agents for X-ray imaging of gastro-intestinal tract.

The invention further relates to dimers of the general formula (II):

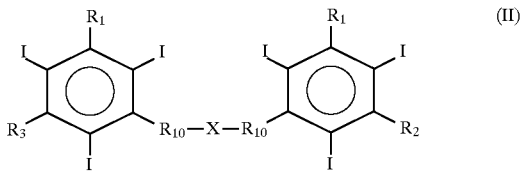

in which $R_1$, $R_2$ and $R_3$ are the same or different, have the same meanings as above, $R_{10}$— are the same or different, are selected among —CO—N($R_4$)—, —N($R_4$)—CO—, —N(COR$_9$)— groups, where $R_4$ has the same meaning as in claim 1 and $R_9$ is an alkyl residue ($C_1$–$C_3$) optionally substituted by 1–2 OH or by alkoxy or hydroxyalkoxy groups, X— is a covalent bond or a linear or branched alkylene chain ($C_1$–$C_8$), which can be substituted by 1–6 OH groups and/or CO—NHR$_4$ groups, and which can be interupted by —O—, —S—, —N—, —N($R_4$)—CO groups, R being the same as above, in which at least one hydroxyl group is esterified with a substituted acrylic acid derivative of formula C(R$_7$)$_2$=CR$_8$—COOH where R$_7$— & R$_8$— are H or (C$_1$–C$_6$) alkyls said acrylic group being in polyacrylic form, i.e. in the form of polymers, homopolymers or copolymers with other olefinic monomers which when suspended in a physiologically acceptable liquid carrier are useful as X-ray contrast agent for the gastrointestinal tract.

Again polymers or homopolymers produced from mixtures of the dimer alone or mixtures of the monomer and the dimer in which the molar ratio of the triiodobenzene compound to the acrylic monomer is between 1:1 and 1:3 are particularly suitable for the manufacture of X-ray contrast agents of the invention. Whether made from monomers alone, dimers alone or mixtures of monomers and dimers in the form of viscous aqueous solutions or gels, the polymerized acrylic esters of triiodobenzenes exhibit high opacification and bioadhesivity.

The invention also relates to a method of making of the compound disclosed by reacting triodo benzene derivatives with acrylic acid derivatives (e.g. as acryloyl chloride) to produce monomers which are subsequently polymerised or copolymerised.

A method of making X-ray contrast compositions for imaging of the GI tract by suspending the polymers of the invention in a physiologically acceptable carrier phase and their use for X-ray imaging of GI tract of human or animal patients is also disclosed.

DETAILED DESCRIPTION OF THE INVENTION

Figure 1:
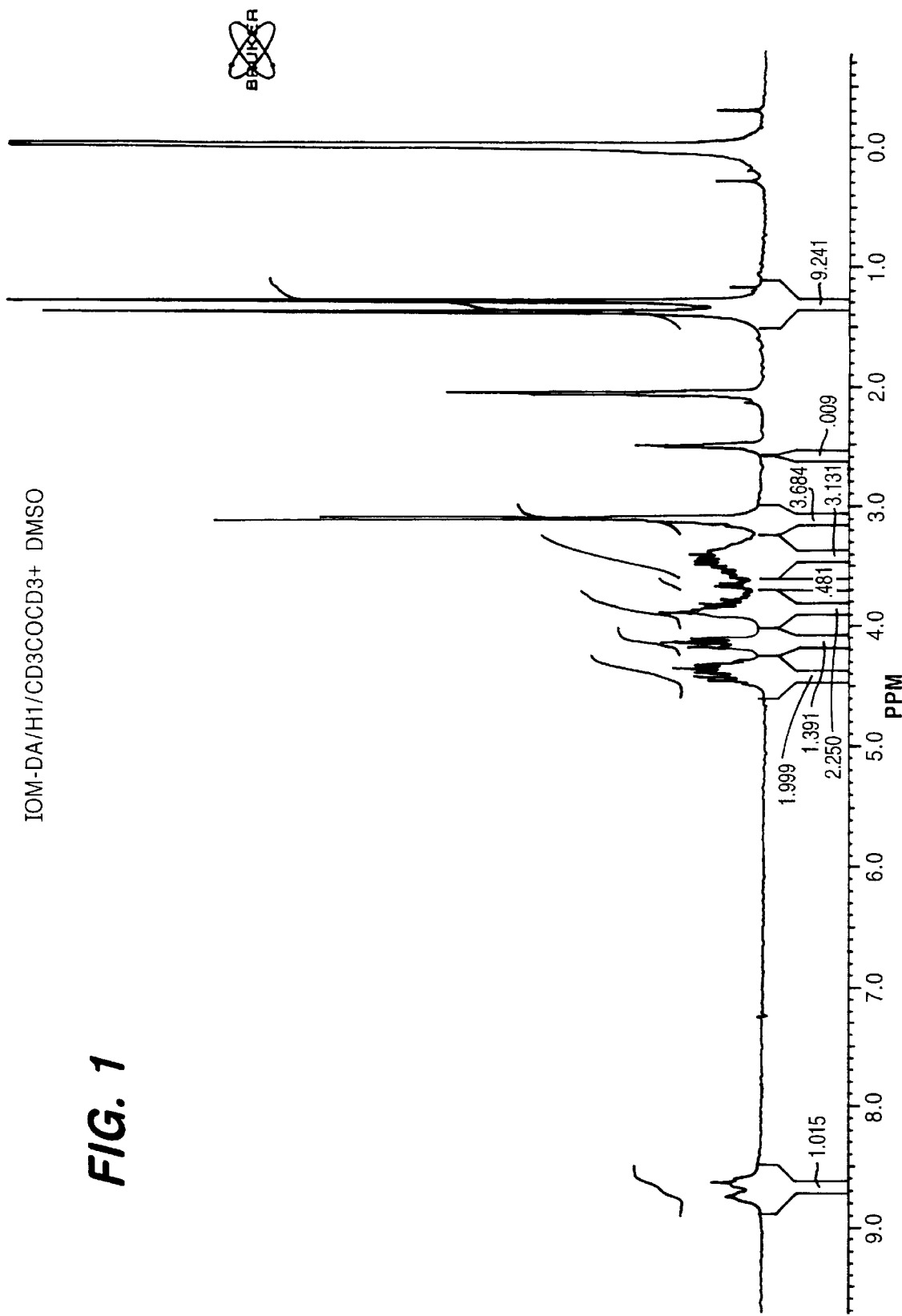
FIG. 1 is an $^1$H NMR spectrum of iomeprol diacetonide.

The main aspect of the invention as set out in the accompanying claims are based on the unexpected finding that when at least one of the hydroxyl groups in the triiodobenzenes of the general formula (I):

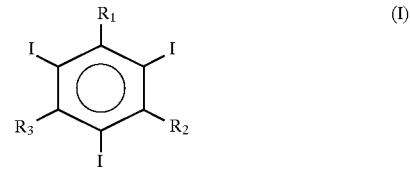

in which $R_1$, $R_2$ and $R_3$ are the same or different and are —CON($R_4$)$R_5$ or —N($R_4$)—CO—$R_6$ groups, where:

$R_4$— is H or a linear or branched alkyl residue ($C_1$–$C_6$), optionally substituted by 1–5 OH and/or alkoxy and /or hydroxyalkoxy groups, $R_5$— is a linear or branched alkyl residue ($C_2$–$C_6$), optionally substituted by 1–5 OH and/or alkoxy and /or hydroxyalkoxy groups or by one or two groups —NH—COR$_5$ or —CO—N($R_4$)R$_5$, or R$_5$ is the residue of a carbohydrate, or $R_4$ and $R_5$ taken together, are alkylene, are an alkylene chain ($C_3$–$C_7$) which can be interupted by O, S, N, $R_6$— is a linear or branched alkyl residue ($C_1$–$C_6$), optionally substituted by 1–5 OH and/or alkoxy and /or hydroxyalkoxy groups and can also include an oxo group, is esterified with an acrylic acid derivative of formula C(R$_7$)$_2$=CR$_8$—COOH wherein R$_7$— & R— are H or an (C$_1$–C$_6$) alkyl group and the resulting non-ionic monomer is polymerized to produce a polymer, copolymer or a homopolymer which when suspended in a physiologically acceptable carrier liquid produces very high opacifications. The polymers showing high level of opacification and bioadhesivity are found particularly useful when used as X-ray contrast agents for gastro-intestinal tract.

To avoid the esterification of too large number of OH groups in $R_1$ and $R_2$ residues some of them in vicinal and adjacent positions can be blocked with a ketone or an aldehyde to produce di-O-isoalkylidene derivative. The ketone can be a dialkyl- and preferably a dimethyl- or diethyl-ketone, thus leading to O-alkylidene-modified compounds. Monoacrylic monomer obtained in this way after polymerisation leads to polymers in which degree of crosslinking is controlled. When the foregoing applies to iopamidol, iohexol or iomeprol, the modified compounds obtained are iomeprol diacetonide, iohexol diacetonide or iopamidol diacetonide of formulae set forth hereinafter.

Amongst the polymers disclosed, particularly useful polymers are polymers and homopolymers of acrylic acid esters of iopamidol, iohexol and iomeprol. The homopolymers of the invention are found to possess high opacification when irradiated with an X-ray source. By homopolymers it is meant the polymer which results from the polymerisation of iodinated acrylic monomers. Other polymers may include copolymers of iodinated acrylic monomers with other olefinic monomers. Other olefinic monomers include acrylic and methacrylic acids and derivatives of such as for instance lower alkyl esters, optionally hydroxysubstituted. Prefered acrylic monomers are acrylic acid, methyl, ethyl, propyl-acrylates, hydroxyethyl-acrylates and methacrylates.

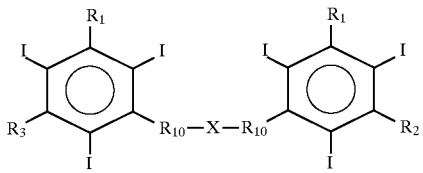

It has also been found that very good results may also be obtained with dimers of the general formula (II) above in which $R_1$, $R_2$ and $R_3$ are the same or different, have the same meanings as in formula I, $R_{10}$— are the same or different, are selected among —CO—N($R_4$)—, —N($R_4$)—CO—, —N(COR$_9$)— groups, where $R_4$ has the same meaning as in claim 1 and $R_9$ is an alkyl residue ($C_1$-$C_3$) optionally substituted by 1–2 OH or by alkoxy or hydroxyalkoxy groups, X— is a covalent bond or a linear or branched alkylene chain ($C_1$-$C_8$), which can be substituted by 1–6 OH groups and/or CO–NHR$_4$ groups, and which can be interupted by —O—, —S—, —N—, —N($R_4$)—CO groups, $R_4$ being the same as above, in which at least one hydroxyl group is esterified with acrylic add group of formula $C(R_7)_2$=$CR_8$—COOH where $R_7$— & $R_8$— are H or an ($C_1$–$C_6$) alkyl group, the resulting non-ionic monomer is polymerized and the resulting polymer or copolymer is suspended in a physiologically acceptable carrier liquid to provide useful X-ray contrast agents for the gastrointestinal tract. Polymers obtained by polymerization or copolymerization of the monomers and/or the dimers of the invention have shown very useful opacifying properties and viscosities compatible with the digestive fluids.

The results have shown that when the X-ray images i.e. X-ray absorption of these compounds is compared to that of the starting material i.e. iopamidol, iomeprol or other triiodobenzenes, the suspensions of homopolymer produces very good images or opacification of the gastric walls. The results have also shown that this finding cannot be explained only by the change in viscosity of the material but that these results are linked to its bioadhesivity. Mixtures prepared using viscous or even bioadhesive compounds such as PVP or Carbopol® with an equivalent amount of iodine containing compounds e.g. iopamidol exhibits opacifications which are below that obtained for the polymers/homopolymers or copolymers of the invention.

Due to their opacification, viscosity and bioadhesivity the polymers and particularly the homopolymers of the invention are almost ideal for use in X-ray imaging of the GI tract. Compositions made with different polymers of the invention have shown to be very effective when used as contrast agents. The effectiveness of the contrast agents made from these compounds comes from the fact that in addition to their capacity to provide good contrast, these compounds exhibit high affinity for the gastrointestinal mucosa and preferably adhere to some areas of the gastro-intestinal mucosa forming luminal linings or coatings improving X-ray absorption patterns. The contrast agents made from these compounds enable improved visualization of specific portions of gastric walls. The fact that the viscosity and bioadhesivity of the contrast agents of the invention may be chosen/adjusted at will provides further advantages for the contrast agents of the invention. The degree of bioadhesivity may be chosen by selecting degree of reticulation (crosslinking) of the acrylic ester polymers used for the contrast agent. Thus experiments with polymers whose degree of reticulation (crosslinking) was relatively low have shown high bioadhesivity while the polymers with higher degree of reticulation have shown lower bioadhesivity.

The reticulation observed is based on the fact that typically (e.g. for iomeprol) there are five reactive sites (five OH) to which acryloyl chloride may be attached and depending on the amount of acryloyl chloride present in the mixture the reaction will proceed on 1, 2, 3, 4 or all 5 sites. Schematically presented the reaction with iopamidol as a triiodobenzene derivative will be as shown on the next page.

The molar distribution between different products i.e. mono-, di-, tri- etc., acrylic acid esters was found to follow Poisson's equation i.e.

$$P(n) = \frac{\mu^n e^{-\mu}}{n!}$$

where P(n) is Poisson distribution, n is degree of substitution (varying from 1–5 in the case of iopamidol) and $\mu$ is a constant dependent on the reaction conditions i.e. kinetics.

A mixture of mono-, di-, tri-, etc. monomers is formed practically in all cases in which all five OH groups are available for the reaction. Subsequent polymerisation of these monomer mixtures yields products

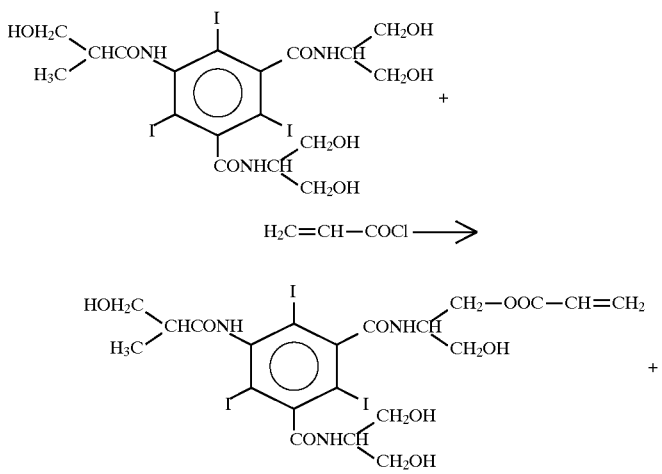

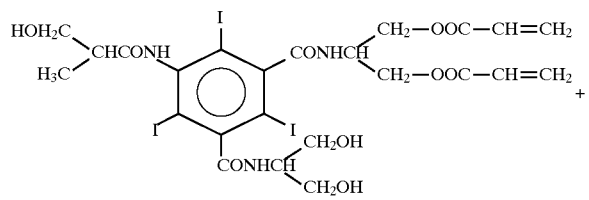

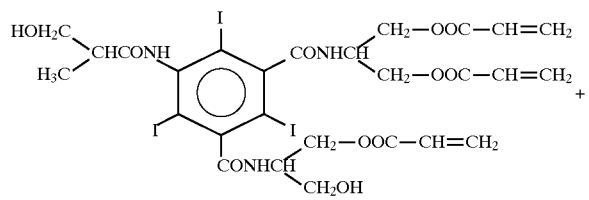

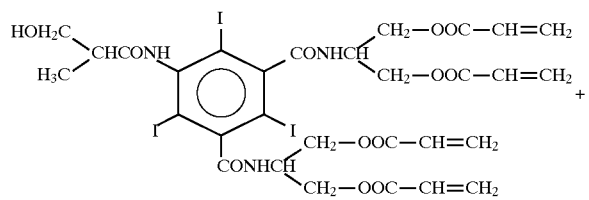

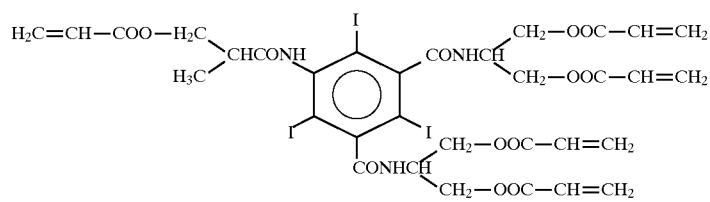

with different degree of reticulation. As the degree of reticulation is directly related to bioadhesivity it was found that by varying the initial conditions of synthesis, water swellable polymers with different degree of bioadhesivity may be produced. Clearly, polymers in the form of viscous fluids or water soluble hydrogels whose bioadhesivity may be selected at will would facilitate the manufacture of contrast agents with custom tailored transit time through the stomach and intestines.

In experiments designed to provide a better understanding and control of the reaction four out of five reactive sites of iopamidol as the triiodobenzene derivative have been blocked (inactivated) by reacting the respective OH groups with acetone to produce iopamidol diacetonide (IOPDA). The diacetonide was then reacted with $CH_2=CH-COCl$ to yield a monomer, monoacryloyl iopamidol diacetonide (ACRIOPDA), according to the reaction scheme:

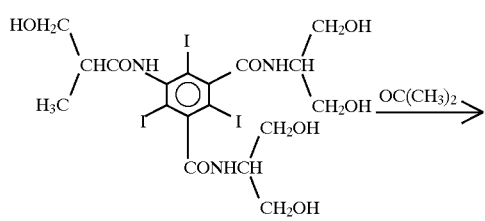

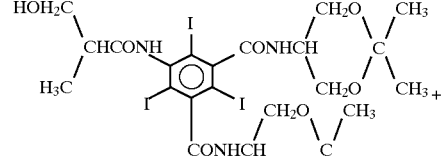

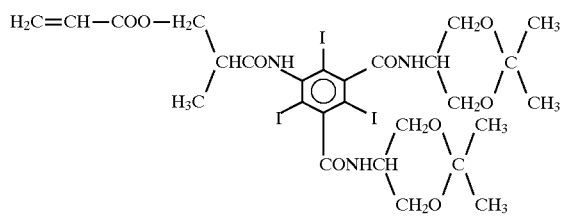

Figure 2:
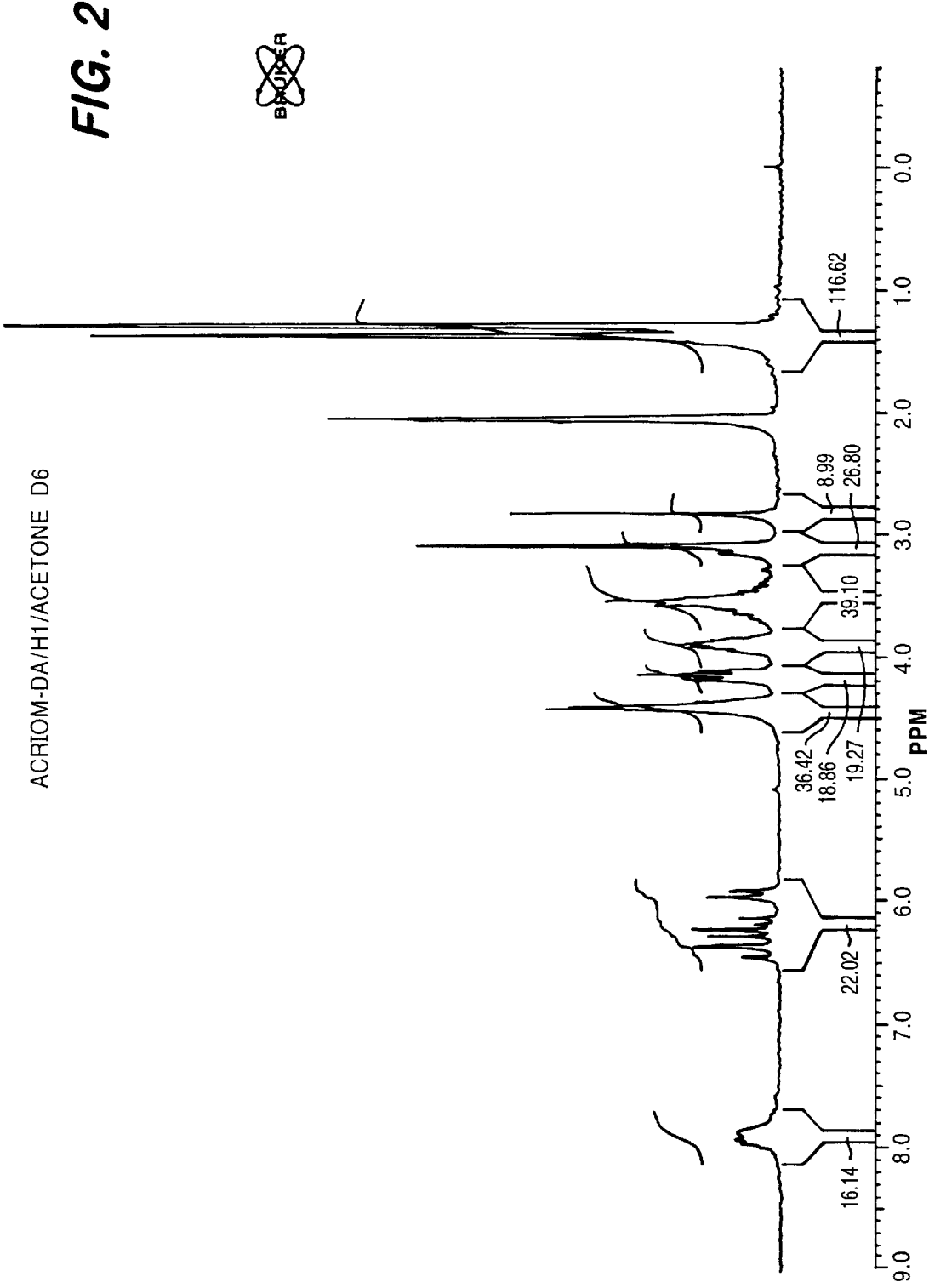
FIG. 2 is an $^1$H NMR spectrum of monoacryloyl diacetonide of iomeprol.
Figure 3:
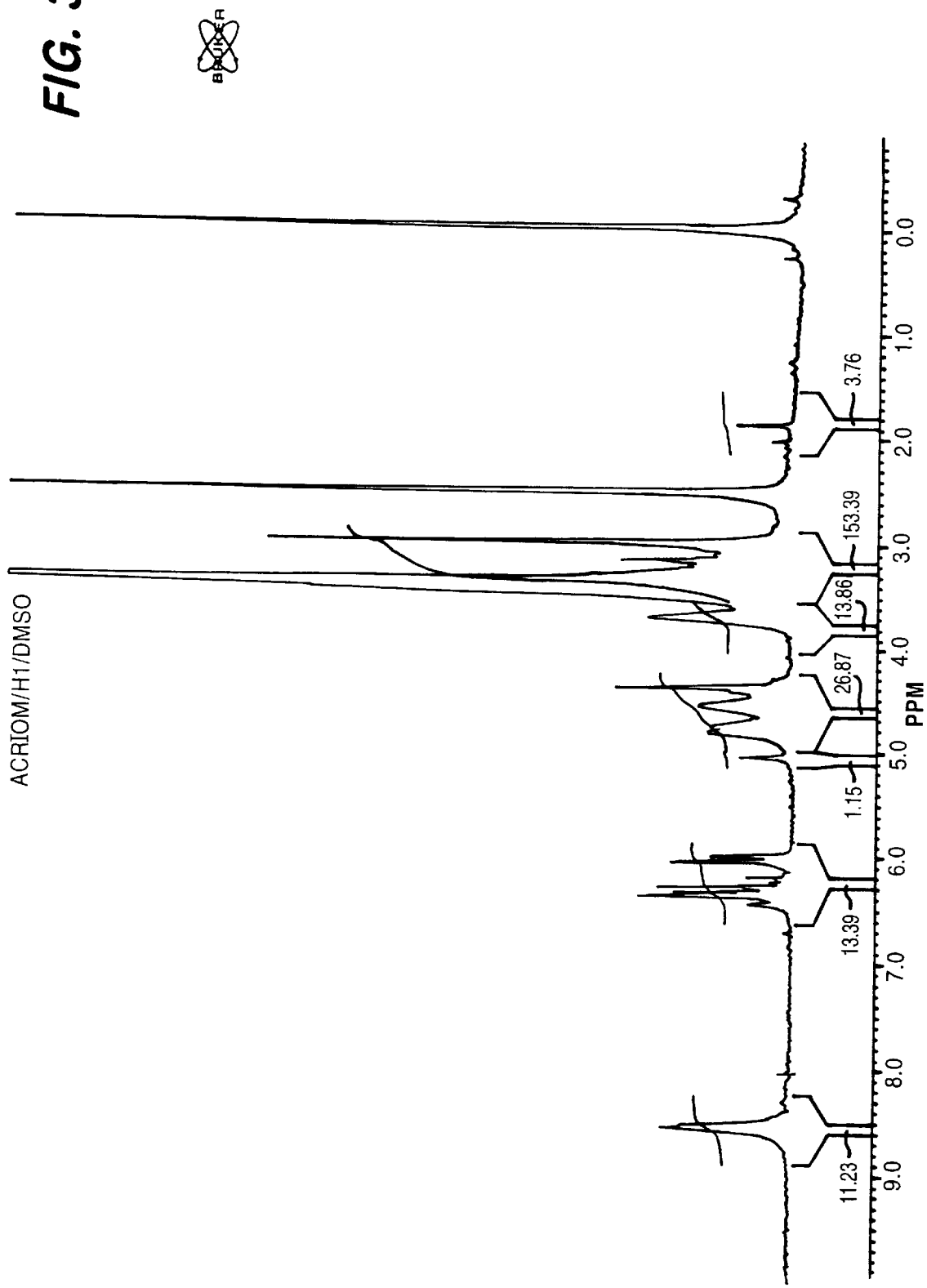
FIG. 3 is an $^1$H NMR spectrum of mono substituted acryloyl triiodobenzene (iomeprol) monomer.

For NMR spectral analysis of various compounds in the scheme see FIGS. 1–3.

After polymerisation the monomer yielded a homopolymer which was not reticulated but which when used as a contrast agent (composition) improved considerably visualisations of lesions and ulcerated areas of gastrointestinal tract.

Interesting properties were observed for polymers comprising a mixture of poly substituted monomer units i.e. mono, di- tri- esters with monomers obtained by inactivation of all but one OH group. These mixed polymers exhibiting varying degree of bioadhesivity and opacification were found to provide an attactive vehicle to X-ray contast agents whose opacification and bioadhesivity may be shifted from high, to medium to low at will. Thus for example a copolymer made from a mixture of monoacryloyl derivative (1 part)/acrylic acid (5 parts)/mixture of acrylic esters (obtained from acryloyl chloride to triiodinated benzene derivatives with initial ratio of 2:1) (0.3 part) provides a polymer whose opacification is that of homopolymer but bioadhesivity is extremely good (i.e. close to that observed for polymers in which the molar ratio of the compound to the acrylic derivative is between 1:1 and 1:3). Obviously by varying the proportions of the constituents and varying the nature (selection) of the starting monomer a large number of X-ray contrast compositions with a range of properties may be produced.

A particular advantage of the contrast agents of the invention resides in the fact that bioadhesive properties as well as degree of opacification of the contrast agent may be chosen/adjusted at will by selecting the acrylic ester polymers with a desired degree of crosslinking (reticulation).

The homopolymer/copolymer of the invention may be produced from any of the monomers or dimers disclosed but are preferably those in which the triiodobenzene derivative is selected from monomers of iopamidol, iomeprol, iopentol, iohexol, metrizamide, iopromide, iogulamide, iosimide, ioversol, ioxilan, iotrolan, ioglunide, ioglucamide, iocibidol, or ioglucol, and dimers such as iodixanol, iodecol, iotrol, iofratol etc. TABLE A & B (page 22–25) lists some of the compounds contemplated. Iopamidol, iohexol and iomeprol as monomers and iodixanol as a dimer are preferred compounds in the Tables A & B.

An orally or rectally administrable X-ray contrast composition of the invention may in addition to one or more polymers, homopolymers or mixture of polymers/copolymers with homopolymers include usual excipients. Thus for example, the contrast composition may include natural or artificial flavourings, fruit juices such as orange juice, sugars and other additives. To preserve isotonicity the polymers are usually formulated with mannitol or xylitol. The contrast compositions of the invention are particularly effective when used in X-ray imaging of the GI tract.

A method of making the compound of the invention by esterification of the triodo benzene derivative with acrylic derivatives such as acryloyl chloride to produce a monomer which is subsequently polymerised or copolymerised. Particularly useful modification of the method is inactivation by a ketone of all except one hydroxyl group of the triiodobenzene derivative prior to esterification with acrylic derivatives. The ketone used may be any dialkyl-ketone but is preferably diethyl-ketone or acetone.

A method of making stable viscous or gelified suspensions of an X-ray contrast composition for imaging of the GI tract by suspending the polymers/homopolymers of the invention in a physiologically acceptable carrier phase.

Use of the composition of the polymers of the invention for X-ray imaging of gastrointestinal tract of human or animal patients and for the manufacture of X-ray contrast agents (compositions) for imaging of oeso-gastro-duodenal tract of human or animal patients.

Use of the polymers of the invention as polymeric filling materials for X-ray monitoring of cavity fillings in the cerebral aneyrism disease is also contemplated.

The following examples further illustrate the invention:

EXAMPLE 1

Acrylic acid esters of iopamidol with different degrees of esterification i.e. molar ratios of acrylic acid/iopamidol were prepared varying the ratio of reactants in the reaction mixture.

7.77 g (0.01 mol) of iopamidol (IOP) were dissolved in 6 g of distilled water at 80° C. Upon dissolution 0.03 mol of $NaHCO_3$ was added and the solution left to cool to 30° C. 0.03 mol solution of acryloyl chloride (2.72 g) (ACR) in chloroform (15 ml) was added dropwise and the resulting mixture stirred with magnetic stirrer for 2 hours at room temperature. Chloroform and any residue of acryloyl chloride was removed by evaporation and the aqueous solution of (ACR/IOP 3/1) ester used for production of polymers.

Esters with 1/1 and 1/2 ratio of iopamidol/acrylic acid were also prepared following the same synthetic route (ACR/IOP 1/1 & ACR/IOP 2/1).

EXAMPLE 2

Esters prepared according to Example 1 were polymerised by heating their aqueous solutions to 90° C. with constant stirring and subsequent addition of a small amount of potassium persulfate as catalyst. The reaction mixtures were then further heated for 15–60 minutes at 80°–90° C. and 150–200 ml of distilled water added to the gels obtained. The gels were passed through Polytron homogeniser and the resulting suspension centrifuged. The undernatants were washed with distilled water until pH~6, dried and then resuspended in 200 ml of water and lyophilised.

TABLE 1

| Acryloyl/<br>Iopamidol<br>mol. ratio | polymer<br>conc.<br>mg/ml | Form | H.U. | mgI/ml<br>determ.<br>by H.U. |
| --- | --- | --- | --- | --- |
| 3:1 | 25 | gel | 669 | 8.2 |
| 2:1 | 25 | gel | 685 | 8.5 |
| 1:1 | 100 | visc. sol | 1923 | 32.5 |

In mixtures with a higher ratio of acrylic acid e.g. 2/1 or 3/1 the polymerisation is almost instant yielding fairly hard gels. In the case of equimolar amounts of iopamidol and acrylic acid the polymerisation was slow (even though more catalyst was added) and the polymer obtained was in the form of a viscous solution rather than a gel. The precipitation of the polymer was therefore in this case carried out in ethanol. Yields of the polymer in all cases were fairly good (between 30–40%) and their iodine content was between 32.8 and 34%. The results obtained by CT scanner analysis of the three polymers are presented in Table 1.

From the results obtained it follows that the most suitable polymer is that made from monomer with equimolar ratio of iomeprol and acrylic acid since highly concentrated (100 g/l) and viscous polymer solutions may be prepared using the polymer. The high viscosity and bioadhesivity of the polymer with high iodine content (34%) makes the polymer of the invention particularly interesting for GI tract radiology.

EXAMPLE 3

Synthesis of IOM-DA 5 g (6.43 mmol) of iomeprol were dissolved in 185 ml of dry acetone, 1.5 g of $FeCl_3$ added and the solution stirred at room temperature. The reaction was followed by thin layer chromatography (TLC) using $CHCl_3/CH_3OH$ 9/1 mixture as the solvent. The reaction was stopped after 25 hours adding 50 ml of 10% solution of $K_2CO_3$, acetone evaporated and the residue extracted with 3×50 ml of chloroform. The choroform solution was then washed with 2×50 ml of distilled water, dried for four hours over $Na_2SO_4$ and filtered. Chloroform was evaporated, the oily residue dissolved in ethyl acetate and the solution left over night at −20° C. to crystallise. After evaporation of the mother liquor the deposit (IOM-DA) obtained was recrystallised in ether, filtered and washed. The yield was 4.6 g or 85.8% and the melting point 235°–238° C. The structure of the compound was confirmed by NMR (see FIG. 1).

Synthesis of IOM-DA ester 4 g (4.8 mmol) of the di-o-isopropylidene-iomeprol (IOM-DA) obtained was partially dissolved in 100 ml of anhydrous dichloromethane. To the solution 800 µl (5.6 mmol) of triethylamine and 0.472 g (5.2 mmol) acryloyl chloride were added. The mixture was stirred at room temperature for 24 hours and reaction followed by thin layer chromatography using $CHCl_3/CH_3OH=9/1$ mixture as the solvent. At the end the reaction mixture was washed three times with water (100 ml), the organic phase dried over sodium sulfate, filtered and dichloromethane evaporated. 3.48 g (81.7%) of the precipitate obtained was washed with 120 ml of ether. The melting point of the white solid precipitate (ACRIOM-DA) was 254°–255° C., Mw=887.25 and iodine content 43% (theoretical). Structure of the acrylic acid ester of the protected iomeprol was confirmed by NMR (see FIG. 2).

Deprotection of inactivated sites 2 g of the ester were dissolved in 80 ml of acetic acid (99%). After dissolution 20 ml of distilled water were added and the reaction in the clear yellow solution obtained, followed by thin layer chromatography using $CHCl_3/CH_3OH$ 9/1 mixture as the solvent. 24 hours later all OH sites of the molecules in the mixture were liberated. 400 ml of distilled water was added, the aqueous solution frozen to −40° C. and lyophilised. 1.87 g of the solid (ACRIOM) were recovered indicating almost 100% yield. Structure was confirmed by NMR (see FIG. 3). The material thus produced was then homopolymerised and/or copolymerised with acrylic acid.

Homopolymerisation

Homopolymerisation of ACRIOM was carried out in substantially the same way as described in the Example 2. 0.5 g of ACRIOM was dissolved in 2 ml of distilled water, the solution heated to 85° C. and to the clear yellow solution small amount of $K_2S_2O_8$ catalyst added. Reaction was fairly rapid and was completed within 15 min. Water was removed, to the viscous deposit left, 25 ml of ethanol were added and the compound precipitated as a light yellow powder. The powder was filtered, washed with ethanol and dried (m=0.4 g). Yield of (ACRIOM)N homopolymer was 80%.

Copolymerisation ACRIOM-AC

ACRIOM was then copolymerised with different amounts of acrylic acid (molar ratio 1:5 & 1:10) following the same procedure. Yields obtained for 1:5 and 1:10 ratio were 54.4% and 48.4% respectively. The polymers showed a slight solubility in organic solvents and formed gels in water (1:10 copolymer gelified rapidly and (ACRIOM)n slowly).

Prior to CT analysis of the compounds produced a calibration curve was obtained by measuring opacification (Hounsfield units) of iomeprol solutions with different iomeprol concentrations (amount of iodine). The calibration "curve" showed a linear relationship of opacification (H.U. units) with the concentration of iodine present in the solution.

TABLE 2

| Polymer (nature) | polymer conc. mg/ml | Form | H.U. | Theor. mgI/ml | mgI/ml obtained by H.U. |
|---|---|---|---|---|---|
| Homopolymer | 25 | gel* | 526 ± 139 | 11.5 | 21 |
| Copolymer 5:1 | 25 | gel | 498 ± 11 | 8.0 | 19.5 |
| Copolymer 10:1 | 23 | gel | 384 ± 35 | 5.7 | 13 |

*Fairly non-homogeneous gel

Water solutions of the homopolymer and the two copolymers were analysed by CT scanner (Picker PQ 1200 SX, kV: 90, mA:35, Filter C, Window 425/215, surface .10 $cm^2$). The results obtained are presented in Table 2.

EXAMPLE 4

Mono-substituted monomer (ACRIOM) produced according to Example 3 was copolymerised with acrylic acid and a "di"-substituted Acryloyl/Iopamidol with molar ratio of 2:1 produced according to the procedure of Example 2. used as a cross-linking agent. Depending on the molar ratio of the ACRIOM monomer, acrylic acid and the cross-linking agent (Acryloyl/Iopamidol: 2/1) viscous solutions or gels of cross-linked copolymers may be obtained exhibiting high opacification and very good bioadhesivity.

EXAMPLE 5

Synthesis of IODIX-DA 10 g (6.45 mmol) of iodixanol (IODIX) were dissolved in 400 ml of dry acetone, 3 g of $FeCl_3$ added and the solution stirred at room temperature. The reaction was followed by thin layer chromatography (TLC) using $CHCl_3/CH_3OH$ 9/1 mixture as the solvent. The reaction was stopped after 25 hours adding 100 ml of 10% solution of $K_2CO_3$, acetone evaporated and the residue extracted with 3×100 ml of chloroform. The choroform solution was then washed with 2×100 ml of distilled water, dried for four hours over $Na_2SO_4$ and filtered. Chloroform was evaporated, the oily residue dissolved in ethyl acetate and the solution left over night at −20° C. to crystallise. After evaporation of the mother liquor the deposit (IODIX-DA) obtained was recrystallised in ether, filtered and washed. The yield was 9.7 g or 88%. The structure of the compound was confirmed by NMR.

Synthesis of IODIX-DA ester 8 g (4.7 mmol) of the di-o-isopropylidene-iodixanol (IODIX-DA) obtained was partially dissolved in 200 ml of anhydrous dichloromethane. To the solution 800 µl (5.6 mmol) of triethylamine and 0.472 g (5.2 mmol) acryloyl chloride were added. The mixture was stirred at room temperature for 24 hours and reaction followed by thin layer chromatography using $CHCl_3/CH_3OH=9/1$ mixture as the solvent. At the end the reaction mixture was washed three times with water (200 ml), the organic phase dried over sodium sulfate, filtered and dichloromethane evaporated. 7 g (84.4%) of the precipitate obtained was washed with 250 ml of ether. Structure of the acrylic acid ester (ACRIODIX-DA) was confirmed by NMR.

Deprotection of inactivated sites 4 g (2.25 mmol) of the ester were dissolved in 160 ml of acetic acid (99%). After dissolution 40 ml of distilled water were added and the reaction in the clear yellow solution obtained, followed by thin layer chromatography using $CHCl_3/CH_3OH$ 9/1 mixture as the solvent. 24 hours later all OH sites of the molecules in the mixture were liberated. 600 ml of distilled water was added, the aqueous solution frozen to −40° C. and lyophilised. 3.95 g of the solid (ACRIODIX) were recovered indicating almost 100% yield. Structure was confirmed by NMR. The material thus produced was then homopolymerised and/or copolymerised with acrylic acid.

Homopolymerisation

Homopolymerisation of ACRIODIX was carried out in substantially the same way as described in the Example 2. 1.5 g of ACRIODIX was dissolved in 6 ml of distilled water, the solution heated to 85° C. and to the clear yellow solution small amount of $K_2S_2O_8$ catalyst added. Reaction was fairly rapid and was completed within 15 min. Water was removed, to the viscous deposit left, 75 ml of ethanol were added and the compound precipitated as a light yellow powder. The powder was filtered, washed with ethanol and dried. Yield of (ACRIODIX)N homopolymer was 87% (1.3 g).

Copolymerisation ACRIODIX-AC

ACRIODIX was then copolymerised with different amounts of acrylic acid (molar ratio 1:5 & 1:10) following the same procedure. Yields obtained for 1:5 and 1:10 ratio were 51.5% and 46.2% respectively. The polymers showed a slight solubility in organic solvents and formed gels in water (1:10 copolymer gelified rapidly and (ACRIODIX)n slowly).

Water solutions of the homopolymer and the two copolymers were analysed by CT scanner (Picker PQ 1200 SX, kV: 90, mA:35, Filter C, Window 425/215, surface 0.10 cm$^2$). The results obtained were similar to those obtained in Example 2.

EXAMPLE 6

(Comparative)

Figure 4:
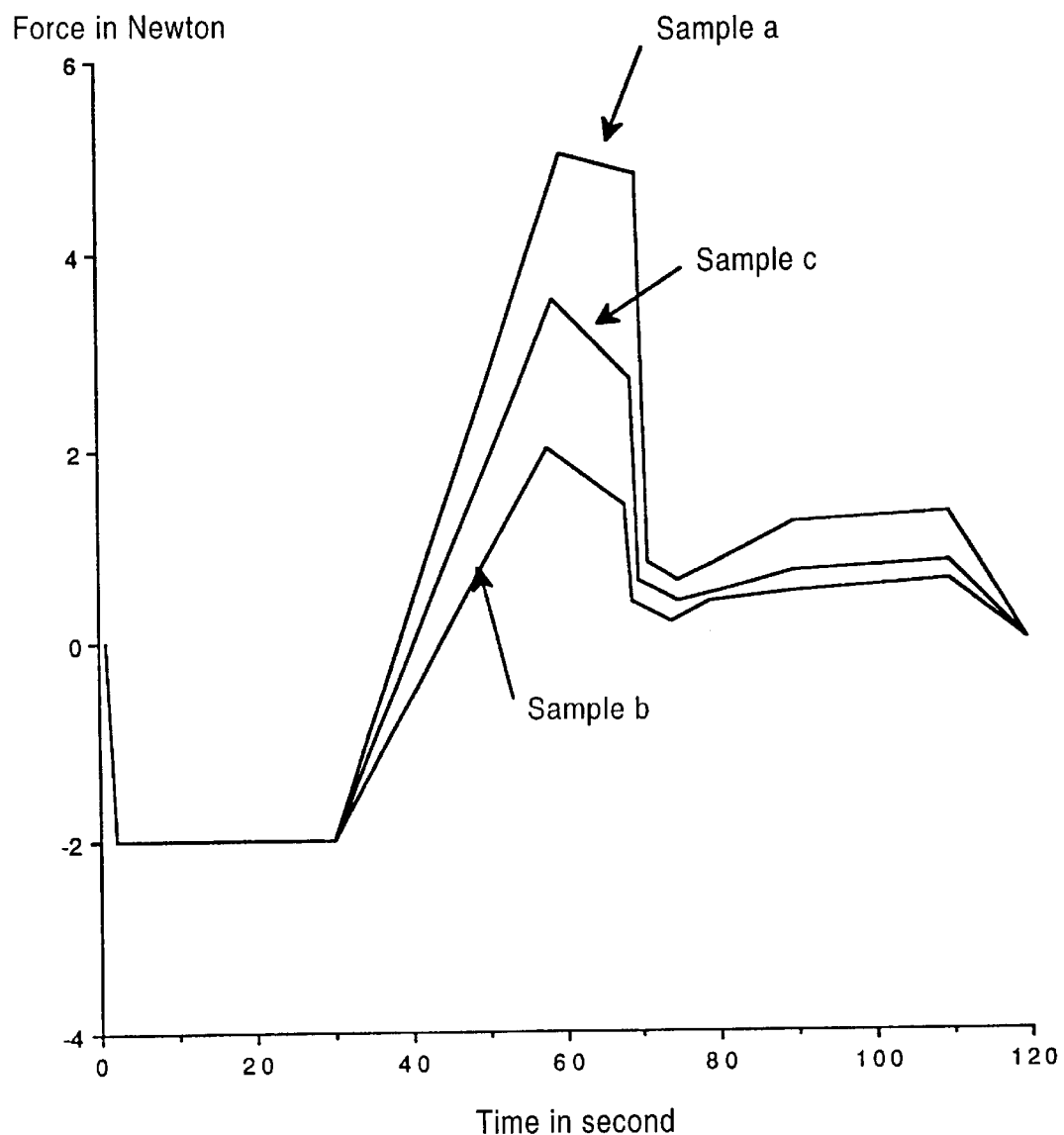
FIG. 4 is a diagram showing a comparative results of bioadhesivity obtained for the polymers of the invention, different triiodobenzene acrylic polymeric derivatives of prior art and of a triiodobenzene derivative in admixture with Carbopol®.

Description of the bioadhesivity test for polymers of the invention (FIG. 4 curve a) polymers of EP-A-0 436 316 (Examples 15, 16 & 18) (FIG. 4 curve b) and admixture of iomeprol with Carbopol® (FIG. 4 curve c).

The bioadhesive bond strength was determined by an in vitro method using a tensile tester (Zwick type 1074) equipped with a custom made cell as described by G. Ponchel et al. Intern. Journ. of Pharmaceutics 38 (1987) 65. Tablets of compressed polymers were attached to the cell with a screw and the internal side of a mouse stomach used as biological tissues. At the beginning of measurement the tablet surface was wetted with 20 μl of water and the wet tablet surface pressed (force=2 Newton) against the biological tissue and kept under these conditions for 30 sec. A constant extension force at the rate of 2 mm/min was then applied at 25° C. and a relative humidity of 60%. The force was recorded as a function of elongation up to the rupture point. The force at the rupture point was recorded and the tested polymers classified. Polymers which showed forces of 5 Newton or better were considered as bioadhesive. The results of these measurements are graphically presented in FIG. 4. From the figure it follows that the polymers of the invention (a) exhibit high bioadhesivity, the polymers prepared according to Examples 15, 16 & 18 of EP-A-0 436 316 (b) show relatively weak bioadhesivity while bioadhesivity of iopamidol/Carbopol mixture (c) was between the two polymers.

EXAMPLE 7

In the experiments reported below, polymer solution was prepared as disclosed in Example 2 (polymer obtained with a acryloyl/iopamidol mole ratio of 1:1), but using $^{125}$I-labelled iopamidol (labeling carried out by CIS-BIOINTERNATIONAL; Gif-sur-Yvette-France). The concentration was adjusted to 30 mg polymer/ml corresponding to about 10 mg iodine/ml. The $^{125}$I-amount in the sample (a) accounted for about 200 000 cpm/ml. The polymer solution also contained 0.3 mmol/ml of mannitol to preserve isotonicity.

Another sample (b) used as control was prepared according to Example 15, 16 & 18 of EP-A-0 436 316 but using $^{125}$I-labelled 5-amino-2,4,6-triodo-isophtalic acid as starting material (Cis BioInternational). Polymer concentration was 60 mg/ml to achieve an iodine concentration of about 10 mg/ml. The $^{125}$I-amount in the sample accounted for about 200 000 cpm/ml. The polymer solution also contained 0.3 mmol/ml of mannitol to preserve isotonicity.

Further sample (c) used as control was prepared by dissolving $^{125}$I-labelled iopamidol in water (20 mg iopamidol/ml i.e. 10 mg iodine/ml) containing 10 mg/ml of Carbopol® 934 (a polymer commercialized from the Goodrich Company) and 0.3 mmol/ml of mannitol.

Five ml of samples a) to c) were administered to Sprague-Dawley rats (about 180–200 g) which were kept fast except for water 24 hours before administration. The samples were introduced intragastrically with a ball-point syringes. The $^{125}$I-tracer amount in each sample accounted for approximately 10$^6$ cpm.

At time intervals of 0.5, 1, 1.5, 2, 3 and 6 hours, animals were sacrified and stomach removed for examination.

Figure 5:
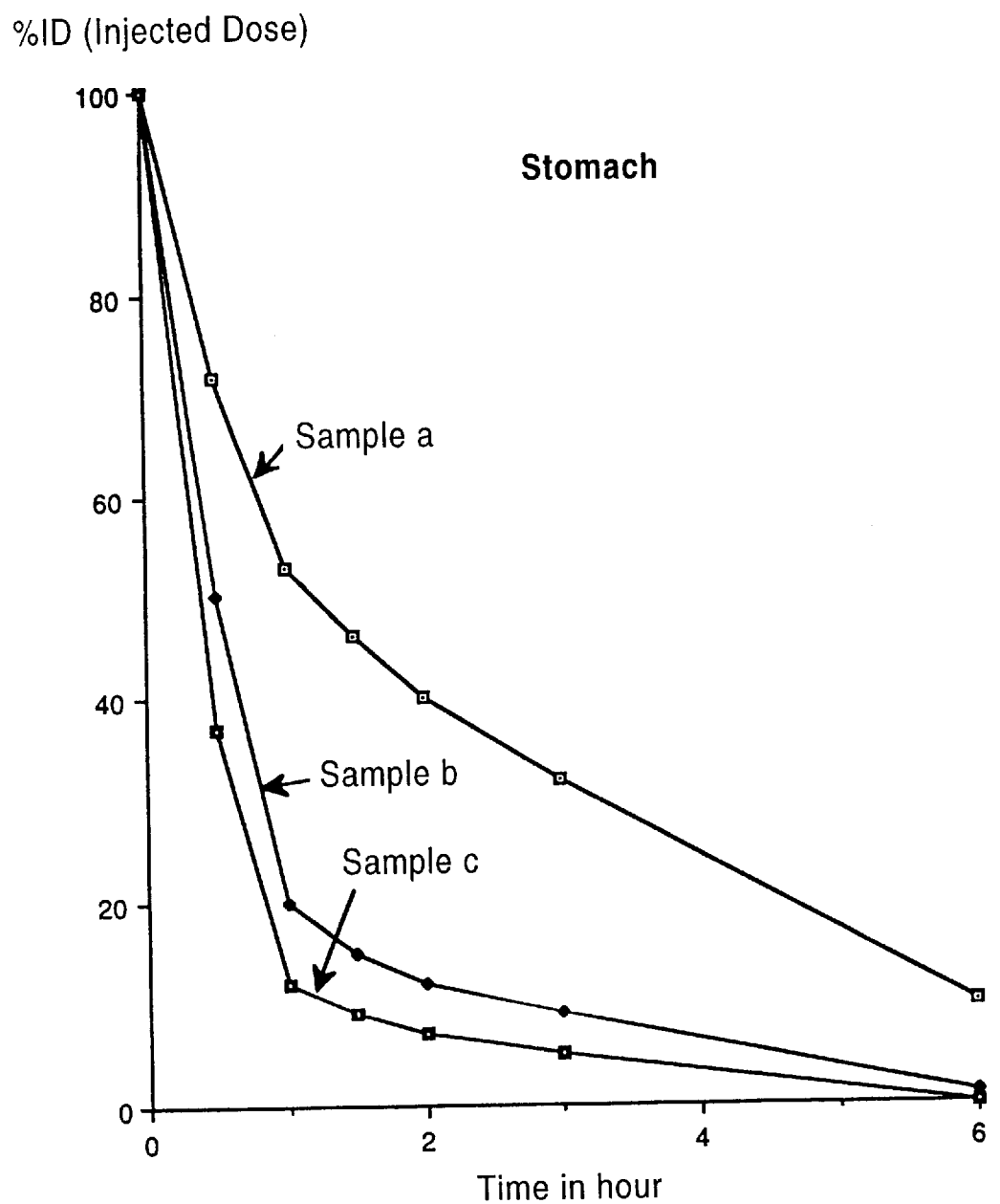
FIG. 5 is diagram showing transit of various triiodobenzene polymers (a & b) and triiodobenzene derivative in admixture with Carbopol® (c) through the stomach of experimental rats.
Figure 6A:
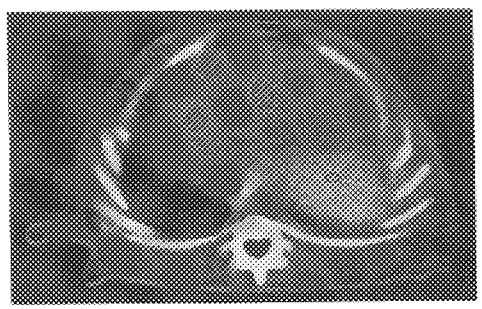
FIGS. 6(a–d) are photographs showing X-ray images of the GI tract of an experimental rat obtained after 10 min, 1 hour, 8 hours, & 24 hours after administration of triiodobenzene polymers of the invention.
Figure 6B:
Figure 6C:
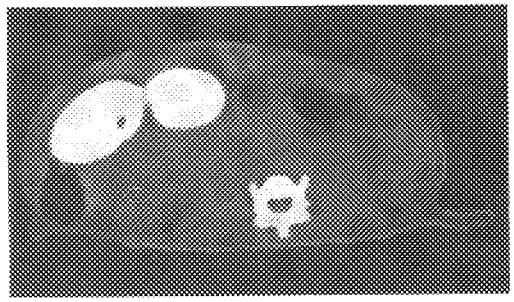
Figure 6D:
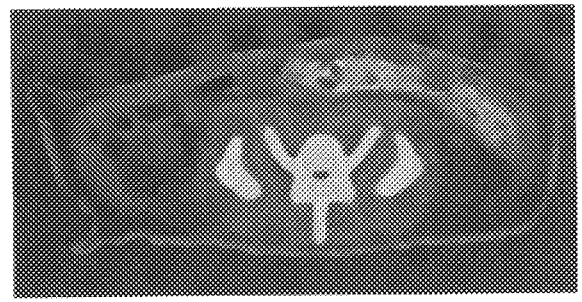

The tests consisted in measuring the radioactive response of the stomach and correlate the results obtained with time. The global results expressed as percentage of the injected dose (%ID) remaining in the stomach as a function of time (presented in FIG. 5) showed that samples b) and c) were similar, i.e. that there was no visible influence of the polymer on the stomach transit time while a) retarded it significantly, thus allowing better opacification and prolonged examination when visualized under CT.

If in the experiments reported in this Example the carrier phases were replaced by mixtures of the component carriers, intermediate transit and retention rates were observed. Hence, the compositions of the invention enable to control the length of the periods during which CT imaging of the digestive tract portions can be performed.

EXAMPLE 8

4.5 ml samples of homopolymers prepared according to Example 3 were administered to OFA female rats (about 180–200 g) which were kept fast except for water 24 hours before administration. The samples were introduced intragastrically with a ball-point syringes and animals scanned by CT scanner (Picker PQ 2000 SX, kV: 130, mA:30, 50 mAs; Scan type axial).

The results recorded are presented in FIG. 6. FIG. 6(a) is the image of the stomach obtained 10 min after administration, FIG. 6(b), is the image of the stomach/pylorus/duodenum obtained 1 hour after administration, FIG. 6(c) is the image of the jejunum/ileum obtained 8 hours after administration, and FIG. 6(d) is the image of the colon obtained 24 hours after administration. These results clearly demonstrate very good opacification and prolonged examination when visualized under CT.

TABLE A

Preferred Monomers

| Generic Name (source) CAS(RN) | $R_1$ | $R_2$ | $R_3$ |
|---|---|---|---|
| Metrizamide (31112-62-6) | —CONHCH(CHOH)$_3$CH$_2$OH<br>\|<br>CHO | —N(Me)Ac | —NH—Ac |
| Iopamidol (60166-93-0) | —CONHCH(CH$_2$OH)$_2$ | —CONHCH(CH$_2$OH)$_2$ | —NHCOCH(OH)CH$_3$ |
| Iomeprol | —CONCH$_2$CH(OH)CH$_2$OH | —CONHCH$_2$CH(OH)CH$_2$OH | —N(Me)COCH$_2$OH |
| Iopromide (73334-07-3) | —CONCH$_2$CH(OH)CH$_2$OH | —CONCH$_2$CH(OH)CH$_2$OH<br>\|<br>Me | —NHCOCH$_2$OMe |
| Ioversol (877771-40-2) | —CONCH$_2$CH(OH)CH$_2$OH | —CONCH$_2$CH(OH)CH$_2$OH | —N—COCH$_2$OH<br>\|<br>CH$_2$CH$_2$OH |
| Iohexol (66108-95-0) | —CONCH$_2$CH(OH)CH$_2$OH | —CONCH$_2$CH(OH)CH$_2$OH | —N—Ac<br>\|<br>CH$_2$CH(OH)CH$_2$OH |
| Iopentol (89797-00-2) | —CONCH$_2$CH(OH)CH$_2$OH | —CONCH$_2$CH(OH)CH$_2$OH | —N—Ac<br>\|<br>CH$_2$CH(OH)CH$_2$OMe |
| Ioxilan (107793-72-6) | —CONCH$_2$CH$_2$OH | —CONCH$_2$CH(OH)CH$_2$OH | —N—Ac<br>\|<br>CH$_2$CH(OH)CH$_2$OH |
| II-1 (99139-49-8) | —CONCH$_2$CH(OH)CH$_2$OH | —N—Ac<br>\|<br>CH$_2$CH(OH)CH$_2$OH | —N—Ac<br>\|<br>CH$_2$CH(OH)CH$_2$OH |
| Iogulamide (75751-89-2) | —CONHCH$_2$CH(OH)CH$_2$OH | —CONCH$_2$CH(OH)CH$_2$OH | —NHCOCO(CHOH)$_3$CH$_2$OH |
| Ioglucol (63941-73-1) | —CONHMe | —NHCOCH(OH)$_4$CH$_2$OH | —N—Ac<br>\|<br>CH$_2$CH$_2$OH |
| Ioglucamide (63941-74-2) | —CONHMe | —NHCOCH(OH)$_4$CH$_2$OH | —NHCOCH(OH)$_4$CH$_2$OH |
| Ioglunide (56562-79-9) | —CONHCH$_2$CH$_2$OH | —NHCOCH(OH)$_4$CH$_2$OH | —N(Me)Ac |
| MP-7011 (76985-84-0) | —CONHCH$_2$(CHOH)$_5$CH$_2$OH | —N(Me)Ac | —NH—Ac |
| MP-7012 (64965-50-0) | —CONHCH$_2$CONHCH(CHOH)$_3$CH$_2$OH<br>\|<br>CH$_2$OH | —N(Me)Ac | —NH—Ac |
| MP-10007 (77111-65-0) | —CONHCH$_2$CH$_2$OH | —NHCOCO(CHOH)$_3$CH$_2$OH | —NHCOCO(CHOH)$_3$CH$_2$OH |
| VA-7-88 | —CONHCHCH(OH)CH$_2$OH<br>\|<br>CH$_2$OH | —CONHCHCH(OH)CH$_2$OH<br>\|<br>CH$_2$OH | —N(Me)Ac |
| (EP 033426) (79944-51-7) | —CONHCHCH(OH)CH$_2$OH<br>\|<br>CH$_2$OH | —CONHCHCH(OH)CH$_2$OH<br>\|<br>CH$_2$OH | —CONHCHCH(OH)CH$_2$OH<br>\|<br>CH$_2$OH |
| Iosimide (79211-10-2) | —CON(CH$_2$CH$_2$OH)$_2$ | —CON(CH$_2$CH$_2$OH)$_2$ | —CON(CH$_2$CH$_2$OH)$_2$ |
| Iocibidol (79211-34-0) | —CONCH$_2$CH(OH)CH$_2$OH<br>\|<br>Me | —CONHCH$_2$CHCH$_2$OH<br>\|<br>OH | —CONH$_2$ |
| (EP 0177414) (103876-29-5) | —N—Ac<br>\|<br>CH$_2$CH(OH)CH$_2$OH | —N—Ac<br>\|<br>CH$_2$CH(OH)CH$_2$OH | —N—Ac<br>\|<br>CH$_2$CH(OH)CH$_2$OH |

TABLE B

Preferred Dimers

| Generic Name (source)CAS(RN) | $R_1$ | $R_2 = R_3$ | $R_{10} - X - R_{10}$ |
|---|---|---|---|
| Iofratol (141660-63-1) | —CONHCH(CH$_2$OH)$_2$ | —NHCOCH(OH)CH$_3$ | —CONHCH$_2$CHCH$_2$NHOC—<br>\|<br>OH |
| Iodixanol (92339-11-2) | —CONHCH$_2$CH(OH)CH$_2$OH | —CONHCH$_2$CH(OH)CH$_2$OH | NCH$_2$CHCH$_2$N—<br>\|    \|    \|<br>Ac   OH   Ac |
| Iotrol (79770-24-4) | —CONHCHCH(OH)CH$_2$OH<br>\\<br>CH$_2$OH | —CONHCHCH(OH)CH$_2$OH<br>\|<br>CH$_2$OH | —NCOCH$_2$CON—<br>\|            \|<br>Me          Me |
| Iotasul (71767-13-0) | —CONCH$_2$CH(OH)CH$_2$OH<br>\|<br>Me | —CONCH$_2$CH(OH)CH$_2$OH<br>\|<br>Me | —NHCOCH$_2$CH$_2$<br>　　　　　　\\<br>　　　　　　S<br>　　　　　　/<br>—NHCOCH$_2$CH$_2$ |
| Iodecol (81045-33-2) | —CONHCH(CH$_2$OH)$_2$ | —CONHCH(CH$_2$OH)$_2$ | —N—COCH$_2$CO—N—<br>\|                          \|<br>CH$_2$CH$_2$OH    CH$_2$CH$_2$OH |
| (WO 92/08691) (143200-04-8) | —CONHCH$_2$CH(OH)CH$_2$OH | —NHCOCH$_2$OH | —CONHCH$_2$CHCH$_2$NHCO—<br>\|<br>OH |
| (WO 92/08691) (143199-77-3) | —CONHCH(CH$_2$OH)$_2$ | —NHCOCH$_2$OH | —CONHCH$_2$CHCH$_2$NHCO—<br>\|<br>OH |
| (WO 92/08691) (143200-00-4) | —CONHCH$_2$CH(OH)CH$_2$OH | —NHCOCH$_2$OH | CH$_2$OH<br>\|<br>—CONHCH$_2$CCH$_2$NHCO<br>\|<br>CH$_2$OH |
| (US 4348377) (78341-84-1) | —CONHCH$_2$CH(OH)CH$_2$OH | —CONHCH$_2$CH(OH)CH$_2$OH | —NHCH$_2$CH$_2$CH$_2$N—<br>\|                        \|<br>COCH$_2$OH    COCH$_2$OH |
| (EP 0308364) (122731-47-9) | —CONCH$_2$CH(OH)CH$_2$OH<br>\|<br>Me | —CONHCH$_2$CH(OH)CH$_2$OH | —NCOCH$_2$CON—<br>\|            \|<br>Me          Me |
| (EP 0308364) (122731-49-1) | —CONHCHCH(OH)CH$_2$OH<br>\|<br>CH$_2$OH | —CONHCH$_2$CH(OH)CH$_2$OH | —NCOCH$_2$CON—<br>\|            \|<br>Me          Me |
| (WO 85/01727) (99139-65-8) | —NCH$_2$CH(OH)CH$_2$OH<br>\|<br>Ac | —NCH$_2$CH(OH)CH$_2$OH<br>\|<br>Ac | —CONHCH$_2$CH$_2$NHCO— |
| (WO 85/01727) (99139-62-5) | —NCH$_2$CH(OH)CH$_2$OH<br>\|<br>Ac | —NCH$_2$CH(OH)CH$_2$OH<br>\|<br>Ac | —CON—CH$_2$CH$_2$NHCO—<br>\|<br>CH$_2$CH$_2$OH |
| (EP 0023992) (78341-84-1) | —CONHCH$_2$CH(OH)CH$_2$OH | —CONHCH$_2$CH(OH)CH$_2$OH | —NCH$_2$CH$_2$CH$_2$N—<br>\|                        \|<br>COCH$_2$OH    COCH$_2$OH |

We claim:

1. A compound of the general formula:

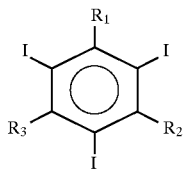

in which $R_1$, $R_2$ and $R_3$ are the same or different and are —CON($R_4$)$R_5$ or —N($R_4$)—CO—$R_6$ groups, where:

$R_4$— is H or a linear or branched alkyl residue ($C_1$–$C_6$), optionally substituted by 1–5 OH and/or alkoxy and/or hydroxyalkoxy groups, $R_5$— is a linear or branched alkyl residue ($C_2$–$C_6$), optionally substituted by 1–5 OH and/or alkoxy and/or hydroxyalkoxy groups or by one or two groups —NH—COR$_5$ or —CO—N($R_4$)$R_5$, or $R_5$ is the residue of a carbohydrate, or $R_4$ and $R_5$ taken together, are alkylene, are an alkylene chain ($C_3$–$C_7$) which can be interrupted by O, S, N, $R_6$— is a linear or branched alkyl residue ($C_1$–$C_6$), optionally substituted by 1–5 OH and/or alkoxy and /or hydroxyalkoxy groups and can also include an oxo group, wherein at least one of the hydroxyl groups is esterified with a substituted acrylic acid group of formula $C(R_7)_2=CR_8-COOH$ wherein $R_7-$ & $R_8-$ are H or $(C_1-C_6)$ alkyls.

2. The compound of claim 1, wherein one or more of the hydroxyl groups are esterified with the substituted acrylic acid group defined in claim 1, and preferably an acryloyl radical.

3. The compound of claim 1, wherein the OH groups in $R_1$ and $R_2$ residues are reacted with a ketone to produce di—O-isoalkylidene derivative.

4. The compound of claim 3, wherein the ketone is dialkyl- and preferably dimethyl- or diethyl-ketone.

5. The compound of claim 4, wherein the compound is iomeprol diacetonide, iohexol diacetonide or iopamidol diacetonide.

6. A non-ionic compound of the general formula:

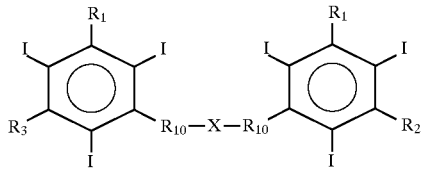

in which $R_1$, $R_2$ and $R_3$ are the same or different, have the same meanings as in claim 1, $R_{10}-$ are the same or different, are selected among $-CO-N(R_4)-$, $-N(R_4)-CO-$, $-N(COR_9)-$ groups, where $R_4$ has the same meaning as in claim 1 and $R_9$ is an alkyl residue $(C_1-C_3)$ optionally substituted by 1–2 OH or by alkoxy or hydroxyalkoxy groups, $X-$ is a covalent bond or a linear or branched alkylene chain $(C_1-C_8)$, which can be substituted by 1–6 OH groups and/or $CO-NHR_4$ groups, and which can be interupted by $-O-$, $-S-$, $-N-$, $-N(R_4)-CO$ groups, $R_4$ being as defined in claim 1, wherein at least one of the hydroxyl groups is esterified with a substituted acrylic acid group of formula $C(R_7)_2=CR_8-COOH$ wherein $R_7-$ & $R_8-$ are H or $(C_1-C_6)$ alkyls.

7. The compound of claim 6, wherein one or more of the hydroxyl groups are esterified with the substituted acrylic acid group defined in claim 1 and preferably an acryloyl radical.

8. The compound of claim 6, wherein the adjacent OH groups in $R_1$ and $R_2$ residues are reacted with a ketone to produce Di-O-isoalkylidene-derivative.

9. The compound of claim 8, wherein the ketone is dimethyl- or diethyl-ketone.

10. The compound of claim 9, wherein the compound is iodixanol diacetonide.

11. A polymer comprising monomer units of the non-ionic compounds of claim 1 or claim 6.

12. The polymer of claim 11, wherein the molar ratio of the triiodobenzene derivative to the acryloyl radical in the starting monomer is between 1:1 and 1:3.

13. The polymer of claims 11, wherein the non-ionic compound is selected from iopamidol, iomeprol, iopentol, iohexol, metrizamide, iopromide, iogulamide, iosimide, ioversol, ioxilan, iotrolan, ioglunide, ioglucamide, iocibidol, ioglucol, iodixanol, iodecol, iotrol, or iofratol, preferably iopamidol, iomeprol, iohexol and iodixanol.

14. The polymer of claim 13, wherein the polymer is a homopolymer comprising recurring units of one of the compounds of claims 5 or 10.

15. An orally or rectally administrable X-ray contrast composition comprising the polymer of claims 11 in an aqueous carrier.

16. A method of making the compound of claim 1 or claim 6, characterized in that prior to acylation with acryloyl radical all except one hydroxyl group of the triiodobenzene derivative are blocked by a ketone.

17. The method of claim 16, wherein the ketone is a dialkyl-ketone preferably diethyl-ketone or acetone.

18. A method of making an X-ray contrast composition for imaging of the GI tract by suspending the polymer of claim 11 in a physiologically acceptable carrier phase containing usual additives and excipients.

19. A method of x-ray imaging of the gastrointestinal tract of a human or animal patient comprising administering to said patient a diagnostically effective amount of the x-ray contrast composition of claim 15.

* * * * *